United States Patent [19]

Baumann et al.

[11] Patent Number: 4,719,808
[45] Date of Patent: Jan. 19, 1988

[54] TEMPERATURE-COMPENSATED ULTRASONIC MEASUREMENT OF WALL THICKNESS

[75] Inventors: Joachim Baumann, Garching; Peter Graf, Riemerling, both of Fed. Rep. of Germany

[73] Assignee: Siemens Aktiengesellschaft, Berlin and Munich, Fed. Rep. of Germany

[21] Appl. No.: 849,403

[22] Filed: Apr. 8, 1986

[30] Foreign Application Priority Data

Apr. 26, 1985 [DE] Fed. Rep. of Germany ........ 3515216

[51] Int. Cl.⁴ ............................................ G01N 29/00
[52] U.S. Cl. ..................................... 73/622; 264/40.1; 425/141
[58] Field of Search ................... 73/597, 622; 264/40.1; 425/141

[56] References Cited

U.S. PATENT DOCUMENTS

| | | | |
|---|---|---|---|
| 3,916,676 | 11/1975 | Boggs et al. | 73/622 |
| 4,137,025 | 1/1979 | Graves et al. | 73/629 |
| 4,346,599 | 8/1982 | McLaughlin et al. | 73/597 |
| 4,520,672 | 6/1985 | Saint-Amour | 73/622 |

*Primary Examiner*—John Chapman
*Attorney, Agent, or Firm*—Hill, Van Santen, Steadman & Simpson

[57] ABSTRACT

An apparatus for measuring the thickness of a tubular plastic layer during the process of its fabrication, which includes an ultrasonic transducer which generates a signal dependent on the thickness of the shape being measured while the shape is at a non-uniform condition of temperature, and circuitry for generating at least one signal from known process parameters, and an arithmetic unit for processing the signals derived as described above to generate an error signal which compensates for the influence of temperature on the test.

5 Claims, 3 Drawing Figures

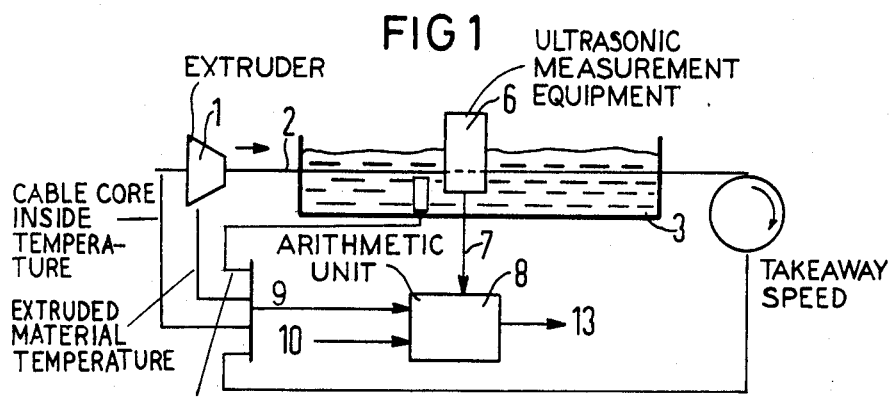
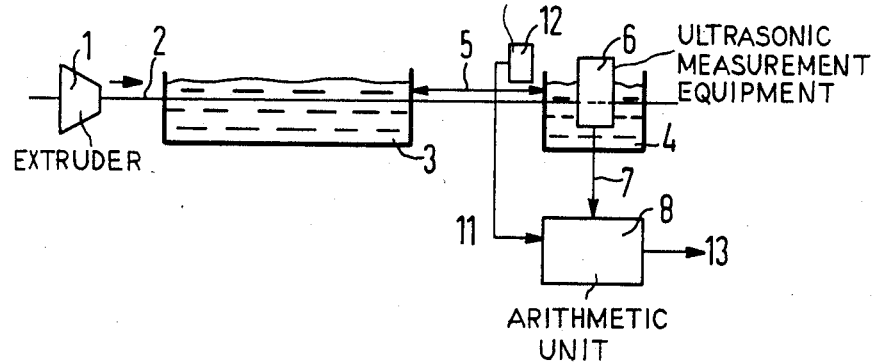
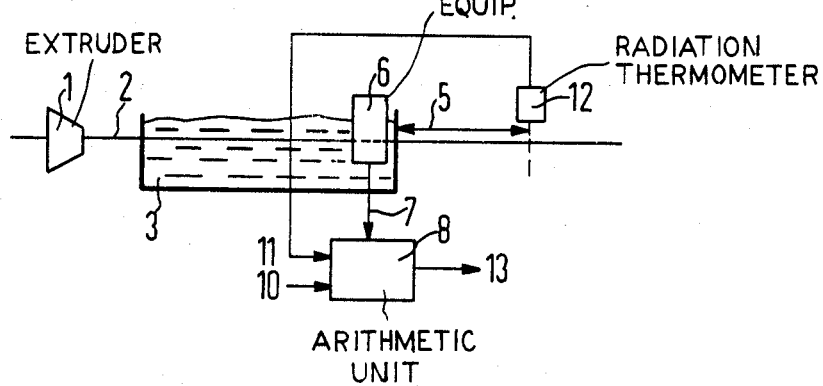

TEMPERATURE-COMPENSATED ULTRASONIC MEASUREMENT OF WALL THICKNESS

BACKGROUND OF THE INVENTION

1. Field of the Invention

The present invention is in the field of apparatus for non-destructive, non-contacting ultrasonic measurement of wall thickness of an extruded plastic tubular shape, provided with means for compensating for non-uniform temperature conditions which would otherwise interfere with the accuracy of the ultrasonic testing.

2. Description of the Prior Art

There is a need in the extrusion of plastic layers for forming cables and lines as well as in the extrusion of plastic pipes and the like to measure directly the thickness of the extruded layer or the wall thickness. Ultrasonic measurements based upon the pulse-echo method provides a suitable measuring procedure. Since the measurement is based on the transit time of the sound wave, the speed of sound in the material under test is a factor in the measured result. For plastics such as polyvinyl chloride, polyethylene, and the like, the sound propagation velocity is temperature dependent to a significant degree. This factor is particularly noticeable when utilizing direct measurement in the manufacturing proces itself followed by the extrusion into a cooling path wherein considerable fluctuations from room temperature as well as additional temperature gradients in the layers to be measured may occur.

If measurements are to be taken at the earliest possible time following the extrusion, a temperature compensation or a correction of the measured thickness values is vital for more precise measurements. In the known ultrasonic measurements of wall thickness used in the manufacture of cables, lines, pipes and the like, the measuring systems make no correction of the measured thickness value on the basis of temperature changes. Therefore, only a limited absolute precision can be achieved in these existing measuring systems, particularly when the temperature gradient is not uniform in the wall layer, but has a specific profile.

The influence of relative process parameters on the ultrasonic measurement can be empirically acquired in tables or constructed functions in a test series. For example, a correction of the ultrasonic measurement is possible with the assistance of a microprocessor but is only approximately possible with limited precision.

In U.S. Pat. No. 3,930,404 there is described a system for measuring dimensions of a tubular article. It employs a pair of ultrasonic transducers which are located diametrically opposite the article in a coupling bath. The tubular article is simultaneously rotated and translated between the transducers to generate a helical inspection path. The transducers direct pulses of ultrasonic energy at the outer tube surface for reflection back to the transducers. Some energy enters the tube wall to the inner tube surface before being reflected back. The signals thus received are electronically processed to provide an indication of the inside and outside diameters and the wall thickness.

SUMMARY OF THE INVENTION

The present invention provides an apparatus for accurately determining wall thickness by ultrasonic means, which formulates and exploits the relevant relationships in the process not only empirically but also physically.

The present invention provides means for determining the temperature behavior with unstable thermal conduction in the layer being measured as well as in the adjacent media. The improvements of the present invention permit a dynamic correction of the measured thickness value for compensating for the influence of temperature. The invention has the advantage that the measurement and evaluation is always directly made and does not depend merely on empirically discovered relationships.

BRIEF DESCRIPTION OF THE DRAWINGS

The present invention will be set forth in more detail by reference to the accompanying drawings in which:

FIG. 1 is a schematic illustration of an extruder, a cooling water bath, and an ultrasonic measuring instrument;

FIG. 2 is a modified form of the invention which employs a further water bath in which the ultrasonic measuring instrument is located; and FIG. 3 is a further modified form of the invention wherein the ultrasonic measuring instrument is situated at the end of the water bath, and is used in combination with a temperature sensor which is downstream of the ultrasonic transducer.

DESCRIPTION OF THE PREFERRED EMBODIMENTS

In FIG. 1, reference numeral 1 indicates generally an extruder which continuously produces a cable 2 or plastic tube of some sort. The extruded plastic tubular shape after extrusion is passed into a cooling water bath 3. An ultrasonic transducer in the cooling water bath is identified at reference numeral 6. The data derived by the ultrasonic transducer 6 is supplied by means of a line 7 to an arithmetic unit 8. Measured values from one or more stages preceding the extruder enter the arithmetic unit 8 through a line 9. Other mathematical equations are introduced into the arithmetic unit 8 through a line 10, and shall be set forth in more detail in a succeeding portion of this specification.

In cases where the temperature of the jacket or sheath of the cable is not directly measurable such, for example, as in the cooling water bath, it must be indirectly identified by mathematical operations of various influencing quantities.

Actuating variables present in the system are constant quantities such as the physical structure of the cable, i.e., the number and shape of the material and the layers contained therein as well as their thicknesses and material constants. The variable, measurable quantities in the fabrication referred to below as process parameters consist of the inside temperature of the cable core, the temperature of the extruded material, the temperature of the cooling water, the cable withdrawal rate and the jacket thickness itself.

For closer definition of the cable temperatures in the course of fabrication, a numerical model of the cable structure including the externally influencing process parameters is compiled. An external computer calculates, off-line, temperature behavior in the cable during cooling and thus receives a temperature profile of the cable jacket at a defined point in time of the cooling phase which corresponds to the location of the ultrasound measurement in the line. Since the speed of sound and its variation with temperature in the jacket material such as polyvinyl chloride or polyethylene is known, the computer uses this temperature profile to identify an averaged speed of sound in the cable jacket which, when multiplied by the sound transit time, yields the wall thickness.

When the actuating variables which depend on the process parameters are varied step-by-step in the model, then the speed of sound dependent on these variables is obtained. The interrelationships thus acquired in point-by-point fashion can be represented as a non-linear equation or can also be represented as an equation system comprising a plurality of variables measurable in the process. This equation or the equation systems are processed on-line by the arithmetic unit 8 during the process.

When the cable core temperature is unknown and not measurable as, for example, in case of a plurality of successive extruding processes, then the additional influence on the jacket temperature can be approximately determined by measuring the surface temperature of the cable outside of the water bath and may be introduced into the calculation.

For fluctuations of process parameters which are not very large from typical mean values, the equation can be made linear about an operating point. The number of process parameters taken into consideration can be reduced or expanded dependent on the quantitative influence of the measuring precision.

The function of the arithmetic unit 8 is to acquire the aforementioned measurable process parameters introduced by the inlet line 9, to solve the equation or equation system introduced at reference numeral 10, and to generate a measured value in various forms which can be used as a control device.

FIG. 1 is an example of this type of system. The insulation or cladding is applied to the line or the cable in the extruder 1. After passing through the extruder, the line or cable proceeds into the water bath 3 for cooling the extruded plastic layer, the ultrasonic transducer instrument 6 also being situated in the water bath 3. The ultrasonic measurement is carried out at the cable or the line which is not yet completely cooled so that a controlled regulation of the extruder can take place within the shortest possible lost time. The plastics temperature required for precise thickness identification and the corresponding speed of sound cannot be directly measured at this location. The above-described method is applied instead.

Turning to FIG. 2, the extruder 1 and the water bath 3 are the same as in FIG. 1. There is provided, however, a second cooling bath 4 separated from the first cooling bath 3 by a free path 5. An ultrasonic measuring instrument in the cooling water bath 4 is identified at reference numeral 6. The values derived by the ultrasonic measuring instrument are supplied by means of a line 7 to an arithmetic unit 8. In FIG. 2, a temperature sensing device such as a radiation thermometer 12 follows the cooling bath 3 and sends its data through a line 11 into the arithmetic unit 8. The corrected value derived from the arithmetic unit 8 is symbolically illustrated at reference numeral 13 in the Figures.

In the system shown in FIG. 2, the cables and lines 2 have a surface exhibiting poor thermal conductivity which emit heat toward the outside so in using a low convection air cooling, in contrast to liquid cooling, no significant temperature gradient arises in the jacket or any existing temperature gradient is eliminated after a short time. The temperature measured at the surface with the temperature sensor 12, such as a radiation thermometer, then reflects the mean jacket temperature reasonably well. The earliest possible point in time or the shortest possible free path illustrated at reference numeral 5 at which the above statement is valid is obtained from the computational simulation of the cooling.

In the system of FIG. 2, no further process parameters need be measured, and the solution of the equations is also eliminated. The only data entering is the formula of the speed of sound dependent on the temperature.

When the ultrasonic measurement is carried out in a water bath 4 immediately following the temperature measuring device 12, the measured surface temperature of the cable will be maintained for a definite time interval long enough for the cable to pass through the ultrasonic measurement equipment. In this case, the jacket temperature at the moment of ultrasonic measurement is known, as is the sonic velocity.

The temperature of the water bath 4 can be easily regulated so it does not rapidly fluctuate.

When the water bath 4 is extremely short, it has practically no influence on the jacket temperature provided there is a fast run-off of the cable and the bath in that case need not be temperature compensated.

An even faster regulation can be achieved by employing a wave coupling of the ultrasonic measuring transducers to the unit under test (not shown) whereby the coupling medium (water) is collected and re-employed in a circulatory manner and is thereby held at the jacket temperature. With wave coupling, the influence of the water on the jacket temperature is even less. However, this type of coupling cannot be easily achieved for some types of units under test.

In cases where an air path for temperature equalizataion must be eliminated for reasons of space, a faster possibility of achieving a nearly equalized jacket temperature is available. The heated fluid bath 4 transmits so much heat to the jacket that the temperature gradient is equalized from the outside.

In order to keep the air of the jacket temperature which is not exactly equalized as small as possible, the temperature of the heated medium should be optimized in accordance with the heat stored in the cable. The fluid medium can also simultaneously be employed as the coupling medium for the ultrasonic measurement.

The system shown in FIG. 3 differs from the systems of FIGS. 1 and 2 in several particulars. In this case, following a free path indicated by reference numeral 5, the mean cable temperature at the end of the water bath 3 can be identified with the outside temperature of the jacket which is measured by the temperature measuring instrument 12. The ultrasonic measuring instrument 6 is therefore positioned at the far end of the water bath. The uncorrected measured values in the line 7 can be converted into the corrected thickness value indicated at a line 13 in the arithmetic unit 8 with the assistance of surface temperature data appearing at the line 11, and measured by the instrument 12 and a correspondingly modified equation or equation system represented at reference numeral 10.

The signal derived as indicated at reference numeral 13 can be used as an error signal to regulate the extruder 1 in accordance the conventional feedback techniques.

It should be evident that various modifications can be made to the described embodiments without departing from the scope of the present invention.

We claim as our invention:

1. A temperature compensated apparatus for non-destructive, non-contacting ultrasonic measurement of wall thickness of an extruded plastic tubular shape which comprises:
   an extruder forming said plastic tubular shape,
   an ultrasonic transducer providing means for generating a first signal dependent on the thickness of said shape while said shape is at a non-uniform condition of temperature,
   a liquid cooling means directly downstream from said extruder,
   means for generating a second signal depending on at least one process parameter, and
   an arithmetic means processing the first and second signals to generate an error signal which compensates for the influence of temperature.

2. An apparatus according to claim 1, wherein said process parameter is at least one of the following:
   inside temperature of said shape, surfce temperature of the layer of extruded material, temperature of the cooling means, withdrawl rate of said shape through said extruder, and thickness of said extruder material.

3. An apparatus according to claim 1, wherein said process parameter is the surface temperature of the layer of extruded material and said cooling means is directly downstream from said extruder, said ultrasonic transducer being located in said cooling means.

4. An apparatus according to claim 1, wherein said process parameter is the surface temparature of the layer of extruded material and said cooling means includes two cooling baths in sequence, said ultrasonic transducer being located in the downstream cooling bath spaced from the upstream cooling bath by a distance sufficient to alter the surface temperature of the plastic tubular shape under test.

5. An apparatus according to claim 1, wherein said process parameter is the surface temperature of the layer of extruded material and said cooling means consists of a single cooling bath, said ultrasonic transducer being located at the far end of said cooling bath in the direction of travel of the shape,
   a temperature sensing means beyond said ultrasonic trasnducer, and
   means for transmitting signals from said temperature sensing means to said arithmetic means.

* * * * *